United States Patent

Chervet et al.

[11] Patent Number: 5,423,513
[45] Date of Patent: Jun. 13, 1995

[54] METHOD OF AND A CAPILLARY FLOW CELL FOR ANALYSING FLUID SAMPLES

[75] Inventors: Jean-Pierre Chervet, Amsterdam; Remco E. J. Van Soest, Bennebroek, both of Netherlands

[73] Assignee: LC Packings International, Amsterdam, Netherlands

[21] Appl. No.: 151,165

[22] Filed: Nov. 12, 1993

[30] Foreign Application Priority Data

Nov. 13, 1992 [EP] European Pat. Off. ........ 92203488.9

[51] Int. Cl.⁶ ............................................. G01N 21/00
[52] U.S. Cl. ............................ 250/227.25; 436/165; 436/172; 422/70; 422/82.08; 422/82.09; 422/58; 73/61.53; 356/411
[58] Field of Search ................. 436/165, 172; 422/58, 422/70, 82.08, 82.09; 250/227.25; 73/61.53; 356/411

[56] References Cited

U.S. PATENT DOCUMENTS

| | | | |
|---|---|---|---|
| 4,548,498 | 10/1985 | Folestad et al. | 356/318 |
| 5,057,216 | 10/1991 | Chervet | 210/198.2 |
| 5,141,548 | 8/1992 | Chervet | 65/108 |
| 5,274,227 | 12/1993 | Moring | 250/227.25 |

FOREIGN PATENT DOCUMENTS

| | | |
|---|---|---|
| 0089157 | 9/1983 | European Pat. Off. . |
| 0396163 | 11/1990 | European Pat. Off. . |
| 2035915 | 2/1971 | Germany . |
| 61/105445 | 5/1986 | Japan . |

Primary Examiner—Robert J. Warden
Assistant Examiner—N. Bhat
Attorney, Agent, or Firm—Young & Thompson

[57] ABSTRACT

A method of analyzing fluid samples using a bent capillary flow cell, in which method an external UV/visible light ray beam is directed into an elongated section of the flow cell from a bend thereof, this incident light ray beam is limited to a solid acceptance angle $\Omega$. This solid acceptance angle $\Omega$ is determined such that light rays which enter the elongated section traverse predominantly the longitudinal axis thereof, i.e. propagate through the fluid sample, providing an improved S/N ratio. Lens means, such as ball lenses, may be used at the entrance and exit side of the elongated section. A bent capillary flow cell is provided, in which the elongated section deviates by an angle $\psi$ from a line N perpendicular to a flat side face of a holding template.

11 Claims, 4 Drawing Sheets

METHOD OF AND A CAPILLARY FLOW CELL FOR ANALYSING FLUID SAMPLES

BACKGROUND OF THE INVENTION

The invention relates to an improved method of and a capillary flow cell for analyzing fluid samples by microseparation techniques such as capillary electrophoresis (CE), micellar electrokinetic capillary chromatography (MECC), electrochromatography (EC), capillary liquid chromatography (LC), supercritical fluid chromatography (SFC), micro high-performance liquid chromatography (micro HPLC) and other related techniques.

CE, for example, is an important alternative and complement to GC and micro-HPLC. In use, a fluid sample is introduced into the flow cell while a UV/visible light ray beam is passed through an elongated section or sample chamber of the capillary flow cell. Light rays travelled through the elongated section are detected by a photo detector or the like and analyzed. The amount of light absorbed by the sample with time provides information about the mass and concentration of solutes contained in the sample, for example.

From U.S. Pat. No. 5,057,216 (Chervet) a bent or curved capillary flow cell is known, having an essentially Z- or U-shaped capillary tubing defining an inner lumen, and an inlet and outlet end for passing fluid samples through the lumen. Between the inlet and outlet ends an elongated section or sample chamber is formed, which connects to a first and second light transmittive bend of the tubing. The elongated section has a longitudinal axis and is positioned in a bore of a template such that the bends extend on either side of the template.

In use, a fluid sample is transported through the lumen of the capillary tubing while a light ray beam as much as possible parallel with the longitudinal axis of the elongated section is incident on the first bend. Light travelled through the elongated section and emanating from the second bend is detected by a detector and analyzed.

A bent capillary flow cell of this type, integrally formed from one piece of tubing, is essentially free of dead volumes. Further, any contact between the fluid sample to be analyzed and light source means and detector means is prevented, because these means are positioned outside the flow cell near its light transmittive bends. This is different from the flow cell disclosed by European patent application 0,089,157 wherein optical waveguides are used for light transmission to and from the elongated section or sample chamber. These optical waveguides, i.e. optical fibers, are fused into the open ends of the chamber to which further inlet and outlet means connect, for passing a fluid sample through the sample chamber.

In the flow cell according to EP-A-0,089,157 the optical waveguides are in direct contact with the fluid sample which can have, inter alia, a detrimental influence on the reliability and accuracy of the analysis because of the possibility of chemical interaction with the fluid.

Further, the connection of the waveguides and the inlet and outlet means to the sample chamber is very cumbersome. This not only because of leakage problems but also in that relatively large dead volumes near these connections are unavoidable. These dead volumes lead to turbulence in the fluid and cause undesired dispersion effects. Because of the risk of fluid leakage, with the use of high voltages in CE of typically 30,000 to 50,000 Volts, safety aspects can not be sufficiently guaranteed for flow cells of the type having fused connections according to EP-A-0,089,157.

Despite its advantages, in particular for analyzing some types of fluids, the signal-to-noise (S/N) ratio of the bent capillary flow cell according to U.S. Pat. No. 5,057,216 is too low for accurate measurement.

SUMMARY OF THE INVENTION

It is an object of the present invention to provide a method of analyzing fluid samples by CE, for example, using a bent capillary flow cell such as a Z- or U-shaped capillary flow cell, which method has an improved S/N ratio. Another object of the invention is to provide a bent capillary flow cell for use with such an improved method.

According to the invention there is provided a method of analyzing fluid samples using a bent capillary flow cell of the type comprising a capillary tubing having an inner lumen, an inlet end and an outlet end for passing fluid samples through the lumen, and an elongated section which connects to at least one light transmittive bend of the tubing between the inlet and outlet ends, this elongated section having a longitudinal axis, wherein the method comprises passing a fluid sample through the flow cell, directing an external light ray beam from the bend into the elongated section, detecting light rays travelled through the elongated section and the fluid sample for analyzing purposes, and wherein the light ray beam is directed onto the bend limited to a solid acceptance angle such that light rays entering the elongated section through the bend traverse predominantly the longitudinal axis of the elongated section.

In the method according to the invention, the incident light ray beam is essentially limited to emit into a solid acceptance angle, such that a fraction as large as possible of the light ray beam traverses the longitudinal axis of the elongated section, i.e. so-called meridional light rays, and interacts with the fluid sample. Light rays incident outside the solid acceptance angle, so-called skew rays, i.e. trapped in the wall of the tubing or evanescing, and which do not contribute to the measurement, are avoided in the method according to the invention.

Due to the higher effective light throughput, the S/N ratio in the method according to the invention is significantly improved as compared to the prior art method using a bent flow cell, which method suffers from a relatively high background noise caused by significant light transmission through the wall of the tubing and shot noise due to a relatively low amount of photons coupled into the fluid sample via the bend of the capillary flow cell.

In order to limit dispersion effects in the optical detection system due to optical power running via different paths in the elongated section, in a further embodiment of the invention the light ray beam is limited to a solid acceptance angle such that light rays entering the elongated section travel predominantly through its lumen.

A further limitation of dispersion effects and accordingly noise in the optical detection system is achieved in a yet further embodiment of the invention, wherein the light ray beam is limited to a solid acceptance angle such that light rays entering the elongated section travel predominantly through its lumen and essentially parallel with the longitudinal axis of the elongated section, i.e. paraxial light rays.

The mentioned solid acceptance angles can be determined by numerical calculations from the cross-sectional dimensions of the tubing and the index of refraction of the material thereof, using known optical ray tracing techniques and/or in an experimental set up, for example.

In case of an essentially parallel light ray beam, in the method according to the invention, the beam is to be directed onto the bend such that the light rays deviate by angle from the longitudinal axis of the elongated section, which angle equals such an angle by which the light ray beam is refracted during its entrance into the capillary flow cell. This refraction angle can also be relatively easily calculated or experimentally determined.

German patent application 2,035,915 discloses a bent or curved cuvette typically used in flow injection analysis (FIA) for coulometric measurements, having an elongated section between a first and second bend of the cuvette. In order to discriminate between a filled (liquid) or empty (air) cuvette, a relatively small parallel light beam is direct onto the first bend of the cuvette and offset from the longitudinal axis of the elongated section, such that an essentially parallel light beam emanates from the second bend and which light beam deviates from the detector in case of an air filled cuvette and is directed towards the detector in case of a fluid filled cuvette.

Besides the different fields of application of the capillary flow cell according to the present application, which is used in microseparation techniques with sample volumes of a few nanoliters, and the cuvette according to DE-A-2,035,915 which is designed for the much larger volumes requiring FIA, the object of the present invention to enhance the S/N ratio by an improved coupling of light into a bent capillary flow cell to increase the number of photons propagating through the fluid sample resulting in a lower noise level, e.g. shot noise, and an improved S/N ratio, is not disclosed nor suggested by DE-A-2,035,915.

In a still further embodiment of the method according to the invention, the light ray beam is limited to the solid acceptance angle through focusing by lens means. By using lens means, reflection of light rays at the entrance of the capillary tubing can be effectively minimized. In order to enhance the S/N ratio even further, in an embodiment of the method according to the invention, the light rays travelled through the elongated section are also focused by lens means, such that essentially only light rays travelled through the fluid are directed to and accepted by a photo sensitive device for analyzing purposes. With these lens means also light rays which have travelled through the fluid sample but are refracted away from the photosensitive device when leaving the tubing can be effectively trapped and directed at the photo sensitive device.

In a preferred embodiment of the method of the invention, in which the elongated section of the capillary flow cell is bounded by first and second spaced bends, the light ray beam is directed onto the first bend and the light rays emanating from the second bend are detected for analyzing purposes.

The method according to the invention can be carried out with any type of bent capillary flow cell, such as the Z- or U-shaped flow cell disclosed by U.S. Pat. No. 5,057,216 provided that the optical interface of the analyzing apparatus with the flow cell is suitably adapted.

In a preferred embodiment, the invention provides also for a bent capillary flow cell, comprising a capillary tubing having an inner lumen, an inlet end and an outlet end for passing a fluid sample through the lumen, an elongated section which connects to first and second spaced light transmittive bends of the tubing between the inlet and outlet ends, the elongated section having a longitudinal axis, and a template having a bore in which the elongated section is positioned such that the bends extend on either side face of the template, the bore is provided such that the longitudinal axis of the elongated section deviates by an angle from a line perpendicular to a side face of the template, in use a light ray beam is to be directed onto the first bend of the elongated section along or parallel with the perpendicular line.

This flow cell configuration has the advantage that it can be used with any type of analyzing apparatus adapted to receive the flow cell known from U.S. Pat. No. 5,057,216. Because of the inclined positioning of the bore of the template, and consequently the inclined positioning of the elongated section of the flow cell, there is generally no need for any modification of the optical system of the apparatus, in order to benefit from the increased light throughput and, accordingly, improved S/N ratio according to the present invention.

In a further embodiment of the capillary flow cell according to the invention, in particular for use with a parallel light ray beam, the deviation or inclination angle equals such an angle by which the light ray beam is refracted during its entrance into the flow cell. This angle can be calculated using ray tracing techniques or can be experimentally determined, for example. By using lens means, positioned outside and in front of at least one but preferably both bends of the flow cell, an optimum alignment of the light ray beam to be directed onto and emanating from the flow cell is achieved.

In another embodiment of the invention a bent capillary flow cell is provided, comprising a capillary tubing having an inner lumen, an inlet end and an outlet end for passing fluid samples through the lumen, an elongated section which connects to first and second spaced light transmittive bends of the tubing between the inlet and outlet ends, the elongated section having a longitudinal axis, a template having a bore in which the elongated section is positioned such that the bends extend on either side of the template, and wherein lens means are positioned outside and in front of at least one of the first and second bends, the lens means for directing a light ray beam onto the first bend being designed for focusing the light essentially limited to a predetermined solid acceptance angle, the lens means for directing light from the second bend to a detector being designed for focusing essentially light rams which have travelled through the fluid sample.

This type of capillary flow cell has also the advantage of fitting into any existing analyzing apparatus suitable for use with the flow cell known from U.S. Pat. No. 5,057,216 and without the need for modifying the optical system of the apparatus for achieving the improved S/N ratio according to the invention.

It has been found that ball lens means provide excellent results. Optimal S/N ratio improvement is achieved by positioning the ball lens means suitably offset from the longitudinal axis of the elongated section. The offset angle and/or distance can be experimentally determined for a given type of flow cell.

The use of fibre optics allows for optimal light ray beam guiding to and from the capillary flow cell in order to achieve an increased light throughput. Further it allows for placing the flow cell separate or remote from the analyzing device which offers new types of applications, e.g. process monitoring, high temperature detection. etc.

Accordingly, in an embodiment of the invention optical fibers are attached to the first and/or second bends of the tubing at the outside surface, or to said lens means, respectively, for light transmission through and/or from the elongated section of the flow cell. When directly attached to the tubing, the optical axis of the fiber has to deviate by an angle from the longitudinal axis of the elongated section of the flow cell. For attaching the fibers UV transparent glue can be used. For highest light throughput the use of tapered fibers is recommended.

In UV detection, flow cells having a sample chamber or elongated section of longer path length exhibit increased sensitivities. If, however, the volume of the flow cell has to be minimized, the cross-section of the lumen must be reduced, resulting in a smaller aperture diameter. It can be shown that for UV detection with cylindrical lumen optimum aperture diameter to length ratios for highest sensitivity have to be within the range of 1/10 to 1/5.

Because of the significantly enhanced light throughput according to the present invention, it is possible to reduce within the optimum range the aperture diameter of the lumen of bent capillary flow cells for low volumes, ranging from 0.2 to 20 nanoliters, for path lengths $\leq 10$ min. This, because with these small path lengths, very small aperture diameters are within reach.

The invention is now described in more detail with reference to the accompanying drawings.

DETAILED DESCRIPTION OF THE EMBODIMENTS

Figure 1:
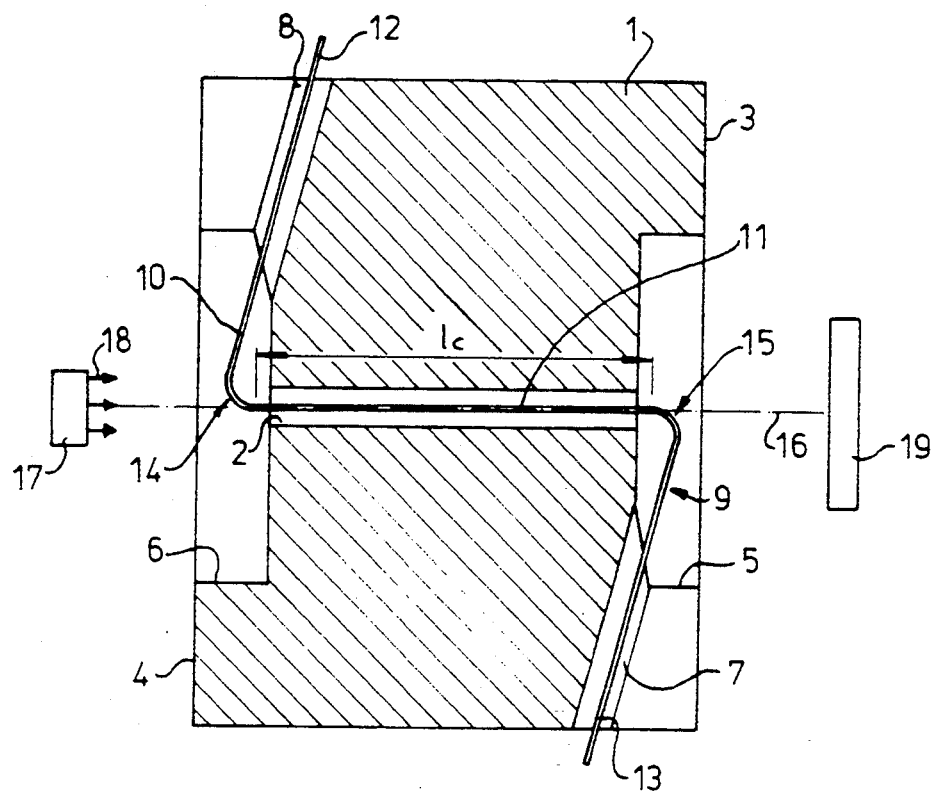
FIG. 1 shows schematically, partially in cross-section, an embodiment of a prior art bent capillary flow cell disclosed by U.S. Pat. No. 5,057,216.

In the figures, equal or comparable parts are indicated by the same reference numerals. The prior art flow cell disclosed in FIG. 1 comprises a template 1, shown in cross-section, having the form of an essentially disc shaped body, with a central through bore 2. Both flat side faces 3, 4 of the template are provided with circular recesses 5, 6 of about half the diameter of the disc and to which narrow radial grooves 7, 8 connect. These grooves 7, 8 ate open to the outer circumference of the template 1. In the embodiment shown, the grooves 7, 8 are mutually offset by 180°, providing a so-called Z-shaped flow cell. In case the grooves 7, 8 are oppositely positioned, a so-called U-shaped flow cell is obtained (not shown).

The disc shape body is preferably made of heat resistant, chemically inert material, such as stainless steel. Also a sandwich construction comprising a cylindrical shim of alumina, for example, on both side faces covered by plastic discs of black polyethylene or Plexiglas, for example, is provided in praxis.

As shown in FIG. 1, through the grooves 7, 8 and the bore 2 a capillary of one piece of tubing 9 extends. The tubing 9 has an inner lumen 10, an inlet end 12 and an outlet end 13 for passing a fluid sample through the capillary. In the bore 2 an elongated or middle section 11 of the tubing 9 extends, bounded by a first bend 14 and a second bend 15. The elongated section 11 has a longitudinal axis 16 which is optimally aligned with the center axis of the bore 2 and includes a right angle with the side faces 3, 4 of the template 1. In other words, the central axis of the bore 2 is parallel with a line perpendicular (normal) to the side faces 3, 4.

The capillary tubing 9 may consist of fused silica coated with polyimide, for example, provided that at least the bends 14, 15 are able to transmit light. Instead of a non-transparent coating, in praxis also transparently coated capillaries have been used or capillaries of which the elongated middle section 11 and the bends 14, 15 are not coated at all.

In use, a fluid sample to be analyzed is passing from the inlet end 12 through the capillary lumen 10 and discharged from the outlet end 13. At the same time a UV or visible parallel light ray beam 18 from a light source 17 is directed onto the first bend 14 of the capillary, parallel with the longitudinal axis 16 of the elongated section 11. A fraction of this light is coupled into the elongated section 11 and travels to the second bend 15. Light emanating from this second bend 15 is detected by a photo sensitive device 19, e.g., a photodiode, for analyzing purposes, for example absorption measurement.

Figure 2:
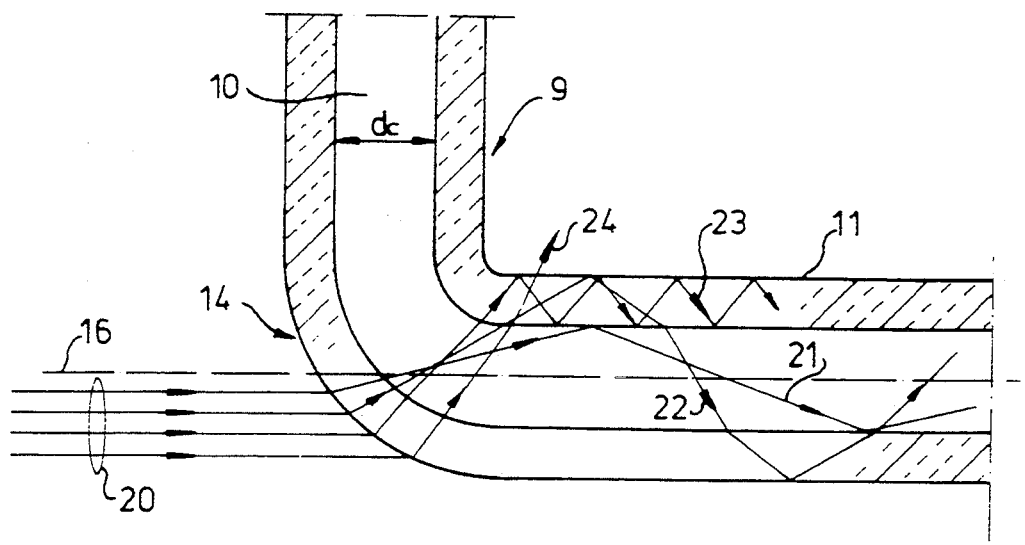
FIG. 2 shows schematically a ray trace analysis of light entering a bend of a capillary flow according to prior art measuring.

FIG. 2 shows, for clarification purposes only, part of the capillary tubing 9 of FIG. 1 on an enlarged scale. According to a prior art method, a collimated light ray beam 20 is incident on the first bend 14 of the tubing 9 parallel with the longitudinal axis 16 of the elongated section 11. As can be seen from FIG. 2, light rays which are coupled into the elongated section 11 propagate along several, different optical paths; i.e. meridional rays 21, 22 which traverse or intersect the longitudinal or symmetry axis 16 of the elongated section 11, the rays 21 of which propagate only through the fluid sample, and skew rays 23, 24 which are not parallel with and do not intersect the axis 16. Skew rays can be trapped inside the wall of the tubing 9, i.e. rays 23, and evanescing or escaping from the tubing 9, i.e. rays 24. Further, some of the incident light rays are reflected at the outer surface of the first bend 14 (entrance). For clarity sake, only four rays have been illustrated.

The rays 21, 22 which traverse or intersect the axis 16 and consequently the fluid sample within the lumen 10 of the elongated section 11 are useful for analyzing purposes, such as absorption measurement. The skew rays 23, 24 do not contribute to the measurement and are the cause of a relatively high background noise at the photo sensitive device 19. Rays parallel to the axis 16 are a special class of meridional rays.

Figure 3:
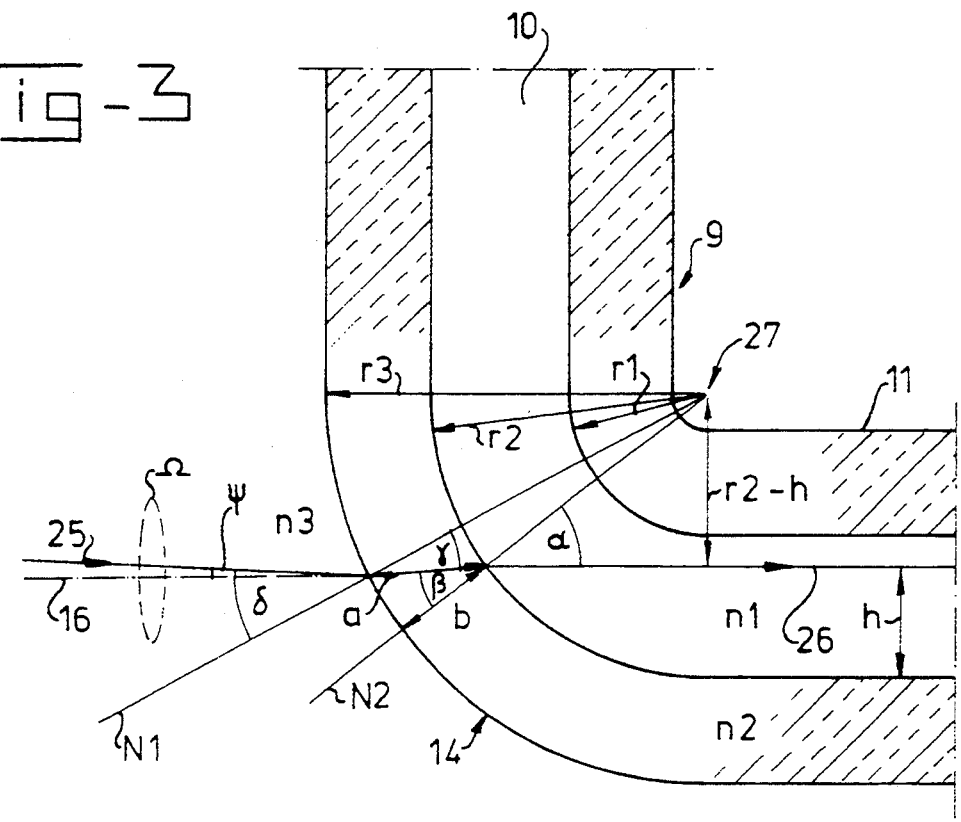
FIG. 3 shows schematically a ray trace analysis of light entering a bend of a capillary flow cell in the method according to the invention.

FIG. 3 shows schematically an example of ray trace analysis for determining a solid acceptance angle $\Omega$ such that light rays entering the elongated section 11 through the bend 14 traverse or intersect predominantly the longitudinal axis 16 of the elongated section 11, according to the present invention.

For calculation purposes, it is assumed that the refraction index of the air, water or matching fluid surrounding the capillary 9 is n3, the refraction index of the tubing is n2 and the refraction index of the fluid sample inside the lumen 10 is n1. With respect to a reference point 27 distances r1, r2 and r3 are assumed, as indicated in the figure. The wall of the tubing 9 has a thickness b. In the figure angles $\alpha$, $\beta$, $\gamma$ and $\delta$ between an incident light ray 25 deviating by an angle $\psi$ from the longitudinal axis 16, and the normals N1 and N2 at the optical interfaces are defined. During entrance, this light ray 25 travels a distance a through the wall of the tubing. Further, the refracted light ray 26 inside the lumen 11 is assumed at a distance h from the inner wall of the tubing 9.

According to Snell's law: $\sin \alpha / \sin \beta = n1/n2$ (1)

from geometric calculation: $\sin \alpha = (r2-h)/r2$ (2)

(2)–(1): $\sin \beta = (n1/n2)(r2-h)/r2$ (3)

further: $b = r3 - r2$ and $a - b/\cos \beta$ (4)

from Snell's law also: $\sin \gamma / \sin \delta = n3/n2$ (5)

and geometrically: $\cos \gamma = (r2^2 - a^2 - r3^2)/(2ar3)$ (6)

further: $\psi = \alpha - \beta + \gamma - \delta$ (7)

and in case of matching: $\psi = \alpha - \beta$ (8)

With the above equations for a given dimension b and known values of the indices of refraction n1, n2 and n3 the angle $\psi$ can be calculated, by which the incident light ray 25 has to deviate from the longitudinal axis 16 in order to produce a refracted ray 26 parallel with the longitudinal axis 16 of the elongated section 11, i.e. a so-called paraxial ray.

From these equations a solid angle $\Omega$ can be determined within which incident light rays are coupled into the elongated section resulting in meridional rays 21 and 22, or only rays 21 travelling through the lumen. i.e. the fluid sample, or just paraxial rays 26, according to the present invention.

Figure 4:
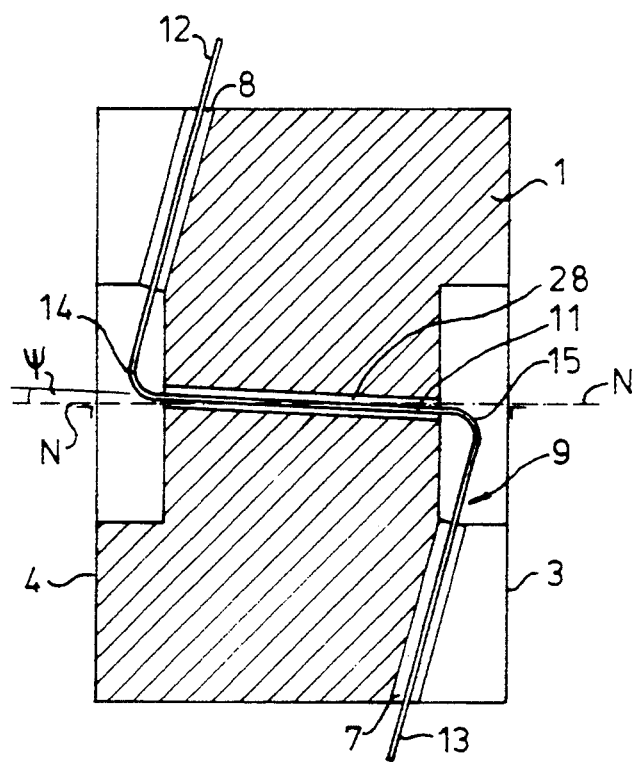
FIG. 4 shows schematically a bent capillary flow cell according to an embodiment of the invention.

FIG. 4 shows a preferred embodiment of a flow cell according to the present invention. Different from the known flow cell shown in FIG. 1, one can clearly see that the bore 28 of the template deviates by an angle $\psi$ from the normal N on the side faces 3, 4 of the template. The angle $\psi$ is determined, according to the invention, such that with an incident coherent light ray beam parallel with the normal N predominantly meridional light rams are coupled into the elongated section 11. It will be understood that such a deviation angle $\psi$ can be determined in that predominantly paraxial light rays will propagate through the elongated section 11, i.e. the fluid sample to be analyzed.

Figure 5:
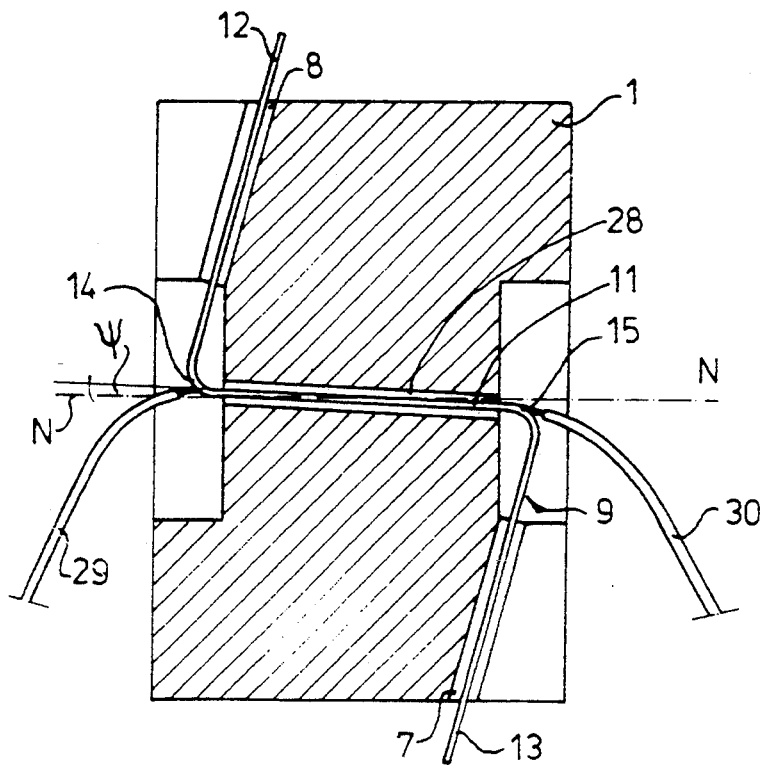
FIG. 5 shows schematically a bent capillary flow cell according to FIG. 4 having optical fibers attached thereto.

FIG. 5 shows a flow cell according to the embodiment shown in FIG. 4, and having optical fibers 29, 30 attached to the tubing 9. Optical fibers 29 is attached with an end to the outside surface of the first bend 14, whereas optical fiber 30 is attached with an end to the outside surface of the second bend 15. For attaching the optical fibers 29, 30 to the tubing 9, UV transparent glue or the like can be used. Because of the deviation of the bore 28 of the template 1 by an angle $\psi$ the optical fibers 29, 30 have to be attached with their respective ends aligned with the normal N on the side faces 3, 4 of the template 1.

It will be clear that the optical fibers 29, 30 can also be used with the flow cell shown in FIG. 1, however the ends of the fibers 29, 30 then have to be attached offset by an angle $\psi$ with respect to the longitudinal axis 16 of the elongated section 11 of the tubing 9, in order to benefit from the enhanced S/N ratio according to the present invention.

Figure 6:
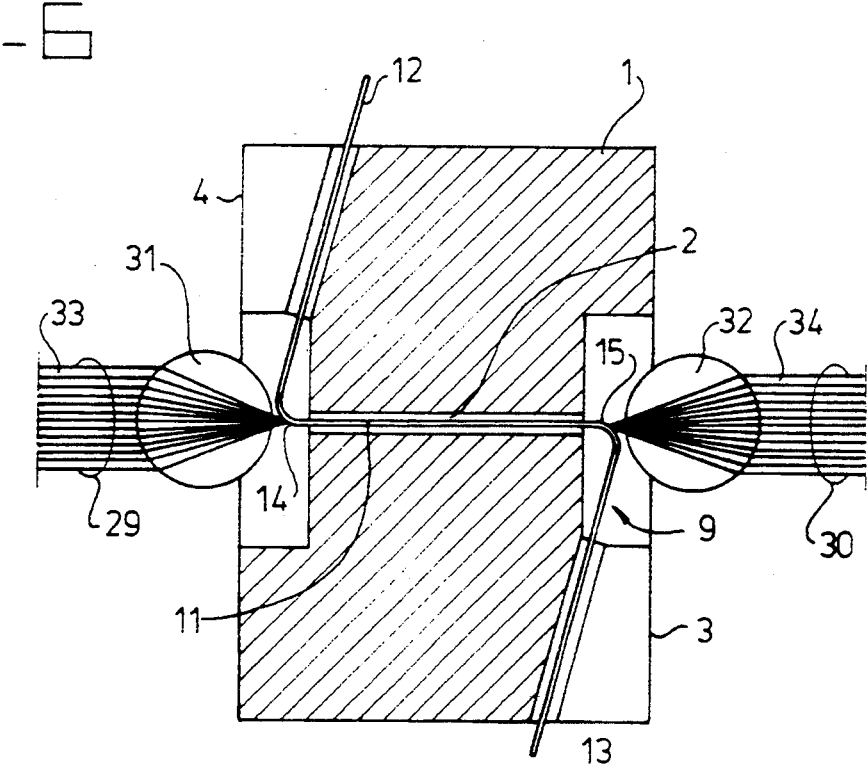
FIG. 6 shows schematically a bent capillary flow cell according to a further embodiment of the invention.

FIG. 6 shows another embodiment of a bent capillary flow cell for use with the method according to the present invention, wherein ball lens means 31, 32 are positioned outside and in front of the first and second bend 14, 15 respectively. These lens means 31, 32 are attached to the template 1 at the circular recesses 5, 6 thereof. Although the use of lenses with the flow cell of FIG. 1 is shown, it will be clear that these lens means 31, 32 can also be used with the embodiment shown in FIG. 4.

The lens means 31 at the first bend 14 of the capillary tubing 9 are designed such that predominantly light is coupled into the elongated section 11 limited to the predetermined solid acceptance angle $\Omega$. Such that as little as possible light is travelling through the wall of the tubing 9 or evanesces. Preferably, the lens means 31 are designed such that mainly paraxial rays are travelling through the elongated section 11. Further, by using lens means, the number of light rays reflected at the outside surface of the bend 14 is reduced, such that a greater amount of light is coupled into the capillary.

The lens means 32 at the second bend 15 of the capillary tubing 9 are designed to focus as little as possible light which has not travelled through the fluid in the elongated section 11, i.e. excluding as much as possible trapped light rays propagating through the wall of the tubing 9, and to trap and direct at the photo sensitive device 19 such light rays 21, 22 and 26 which have travelled through the fluid sample but which are refracted away from the photo sensitive device during their exit at the second bend 15. This to obtain a very low background noise level at the photo sensitive device.

Preferably both lenses 31, 32 are used, but with only the lens means 31 a significant improvement over the prior art measurement can be obtained already. The light beam 33 from an external light source can be incident on the lens means 31 through an optical fiber 29 attached thereto, whereas the light beam 34 focused by the lens means 32 may be guided to a photo sensitive device via an optical fiber 30 attached to the lens 32.

Figure 7:
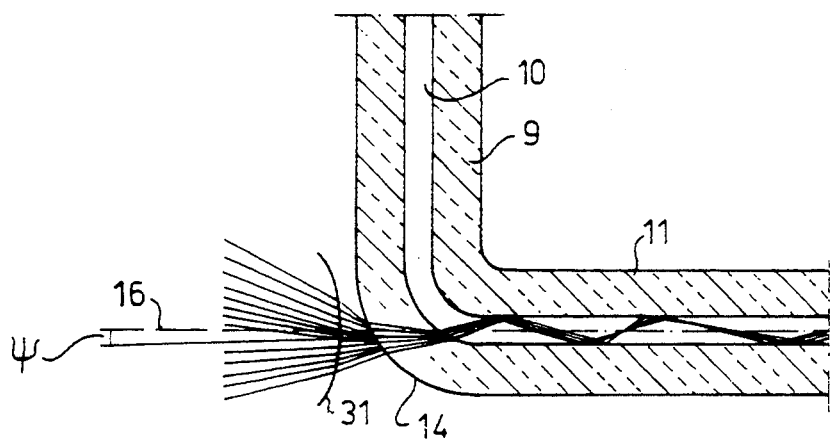
FIG. 7 shows on an enlarged scale detail of the flow cell according to FIG. 6.

FIG. 7 illustrates on an enlarged scale the positioning of the lens means 31 with respect to the first bend 14 of the tubing 9. The lens 31 is positioned such that the focused beam deviates by an angle $\psi$ from the longitudinal axis 16 of the elongated section or sample chamber 11 of the flow cell. Although ball lens means are preferred, the invention is not limited to such lens means.

Figure 8:
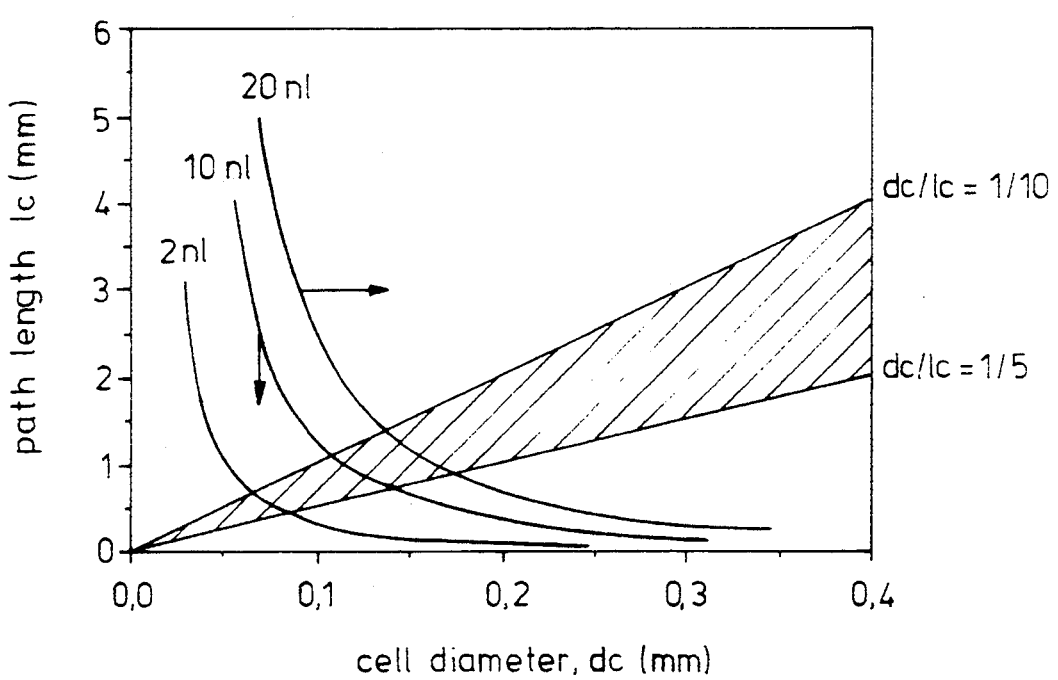
FIG. 8 shows diagrammatically the optimum range for the aperture-to-length ratio of cylindrical flow cells.

FIG. 8 shows a plot of the ratio dc/lc of the aperture diameter dc of the lumen 10 and the path length lc of the elongated section 11 of cylindrical cells with volumes ranging from 0.2 to 20 nanoliters, see also FIGS. 1 and 2. Both Z- and U-shaped bent capillary flow cells can be considered as cylindrical cells and should be constructed with respect to optimal aperture ratio, indicated by the shaded area in FIG. 8. The arrows in the figure indicate the directions for aperture optimization. For highest sensitivity the ratio dc/lc should have numbers within the range of 1/10 to 1/5, for values below 1/10 the utilizable light energy rapidly decreases, resulting in increased noise and poor linearity. For values above 1/5 the path length becomes too short, resulting in poor sensitivity. The substantial decrease of 5 to 10 fold in noise from using flow cells with path lengths $\leq 10$ mm counterbalance the drawbacks of loosing some of the sensitivity (about a factor 2) versus capillary flow cells of 20 mm path length. Further, the risk of zone overlap and dispersion in the elongated section of the capillary flow cell is significantly reduced with flow cells of shorter path length.

With the improved light coupling according to the present invention, it is possible to provide flow cells for volumes ranging from 0.2 to 20 nanoliters with path lengths lc $\leq 10$ mm within the optimum range indicated in FIG. 8.

The thickness of the template 1, i.e. the distance between the side faces 3, 4 depends on the desired optical path length of the cell. In present flow cells, the thickness of the template is $\leq 10$ mm, the central bore 2, 28 has a diameter of about 0.1 mm to 1.6 mm and the circular recess 5, 6 have a width of about 16 mm. The grooves 7, 8 have a width of about 0.5 mm. These dimensions may, of course, vary dependent on a specific design and measurement. The inner diameter or aperture diameter dc of the lumen 10 of the tubing 9 should not exceed 200 $\mu$m, otherwise dispersion in the detector affects the efficiency of the separation. For capillary SFC or CE smaller internal diameters (I.D.) e.g. $\leq 75$ $\mu$m are required.

The cell according to the invention can be manufactured in the same manner as disclosed by the prior art from coated or uncoated fused silica. The lens means 31, 32 are preferably quartz material.

With an optimized flow cell and method according to the present invention, the sensitivity of bent capillary flow cells in terms of signal-to-noise (S/N) values can be significantly improved. Sensitivity enhancement of at least a factor 10 and even more are possible, resulting in lower limits of detection of the same magnitude. Such an optimized flow cell can be used at an even wider field of application.

The inventive idea of the present invention is, of course, not limited to the embodiments shown or discussed.

We claim:

1. A bent capillary flow cell comprising a capillary tubing having an inner lumen, an inlet end and an outlet end for passing fluid samples through said lumen, an elongated section which connects to first and second spaced light transmittive bends of said tubing between said inlet and outlet ends, said elongated section having a longitudinal axis, and a template having side faces and a bore in which said elongated section is positioned such that said bends extend on either side face of said template, wherein said bore is located in said template such that the longitudinal axis of said elongated section deviates by a deviation angle from a line perpendicular to a side face of the template, whereby in use, a light ray beam is to be directed onto the first bend of the elongated section along or parallel with said perpendicular line.

2. A bent capillary flow cell according to claim 1, wherein said deviation angle equals an angle by which the light ray beam is refracted during its entrance into the capillary flow cell.

3. A bent capillary flow cell according to claim 1, wherein optical fibers are attached to either one of said first and second bends, at their outside surface, for light transmission through and from said elongated section.

4. A bent capillary flow cell according to claim 1, comprising lens means positioned outside and in front of at least one of said first and second bends.

5. A bent capillary flow cell according to claim 4, wherein said lens means comprise ball lens means.

6. A bent capillary flow cell according to claim 5, wherein said ball lens means are positioned offset from the longitudinal axis of the elongated section.

7. A bent capillary flow cell according to claim 4, wherein optical fibers are attached to either one of said lens means, for light transmission through and from said elongated section.

8. A bent capillary flow cell according to claim 1, comprising lens means positioned outside and in front of both said first and second bends.

9. A bent capillary flow cell according to claim 1, wherein the length of the elongated section is less than 10 mm, and the ratio of the aperture diameter of the lumen to the length of said elongated section is within the range of 1/10 to 1/5.

10. A bent capillary flow cell comprising a capillary tubing having an inner lumen, an inlet end and an outlet end for passing fluid samples through said lumen, an elongated section which connects to first and second spaced light transmittive vends of said tubing between said inlet and outlet ends, said elongated section having a longitudinal axis, and a template having side faces and a bore in which said elongated section is positioned such that said bends extend on either side face of said template, wherein optical fibers are attached to said first and second bends, at their outside surface, for light transmission through and from said elongated section, said optical fibers having their optical axis deviated by an angle from the longitudinal axis of said elongated section.

11. A bent capillary flow cell according to claim 10, wherein the length of the elongated section is less than 10 mm, and the ratio of the aperture diameter of the lumen to the length of said elongated section is within the range of 1/10 to 1/5.

* * * * *